United States Patent

Vallelunga et al.

[11] Patent Number: 5,290,255
[45] Date of Patent: Mar. 1, 1994

[54] APPARATUS FOR SHIELDING A SYRINGE NEEDLE

[76] Inventors: Anthony J. Vallelunga, 209 Schoolhouse Rd., Albany, N.Y. 12203-5956; Paul V. Cacciotti; Vincent E. Cacciotti, both of 9 Morgan Way, Latham, N.Y. 12110

[21] Appl. No.: 12,309

[22] Filed: Feb. 2, 1993

[51] Int. Cl.⁵ ............................................. A61M 5/32
[52] U.S. Cl. ..................... 604/197; 604/110; 604/195; 604/198; 604/192
[58] Field of Search ............ 604/110, 187, 192, 195, 604/197–199, 263, 207, 218, 189

[56] References Cited

U.S. PATENT DOCUMENTS

| | | | |
|---|---|---|---|
| 4,135,510 | 8/1982 | Maszkiewicz | 604/195 |
| 4,666,435 | 5/1987 | Braginetz | 604/198 |
| 4,743,233 | 5/1988 | Schneider | 604/192 |
| 4,871,355 | 10/1989 | Kikkawa | 604/198 |
| 4,923,445 | 5/1990 | Ryan | 604/195 |
| 4,923,447 | 5/1990 | Morgan | 604/198 |
| 4,935,016 | 6/1990 | Deleo | 604/198 |
| 4,998,920 | 3/1991 | Johnson | 604/198 |
| 5,024,616 | 6/1991 | Ogle, II | 604/192 |
| 5,059,185 | 10/1991 | Ryan | 604/198 |
| 5,098,403 | 3/1992 | Sampson | 604/198 |
| 5,197,953 | 3/1993 | Colonna | 604/110 |

FOREIGN PATENT DOCUMENTS 2079607 1/1982 United Kingdom .......... A61M 5/00

OTHER PUBLICATIONS

Janine Jagger, et al., New England Journal of Medicine, 319: 284–288 (1988).
Susan Doan-Johnson, Nursing92, p. 24 and p. 27, Aug. 1992.
Kathy Bowles and Mary Lynch, RN, pp. 42–45, Jul. 1992.
Accidental Needle Sticks, product literature for Monoject Safety Syringe of Sherwood Medical Company, (St. Louis, Mo.) 1992.

Primary Examiner—C. Fred Rosenbaum
Assistant Examiner—Vanitha Alexander
Attorney, Agent, or Firm—Heslin & Rothenberg

[57] ABSTRACT

A needle shield and syringe assembly are provided. The main components of the needle shield are a hollow sleeve, a needle shielding means, and a snap ring. Radially extending protrusions are provided on the hollow sleeve, which slide within longitudinally extending slots in the needle shielding means allowing extension and retraction of the needle shielding means. The snap ring is positioned within a groove in the hollow sleeve at retraction, and extends into a groove in the needle shielding means at extension. Extension of the snap ring into the groove in the needle shielding means locks the shield in the extended position over the syringe needle.

9 Claims, 3 Drawing Sheets

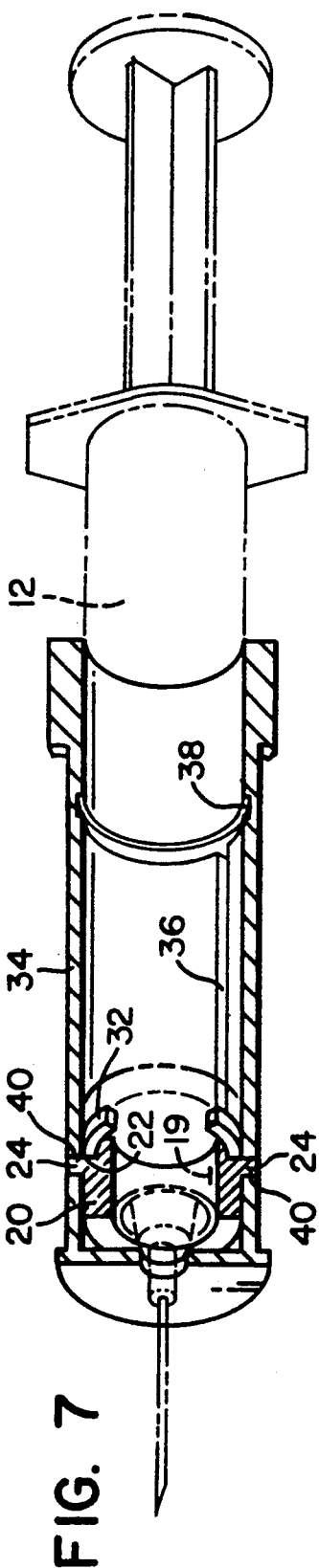
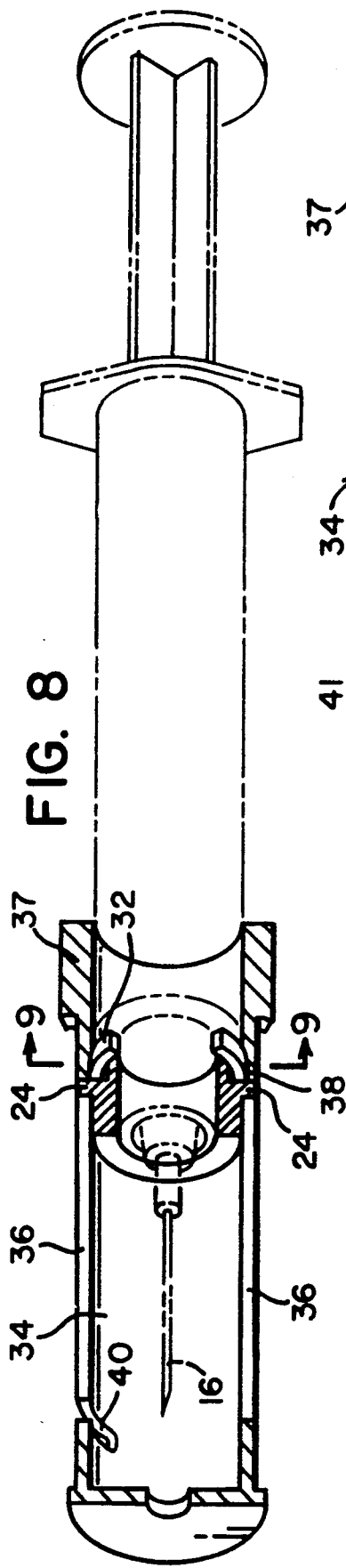
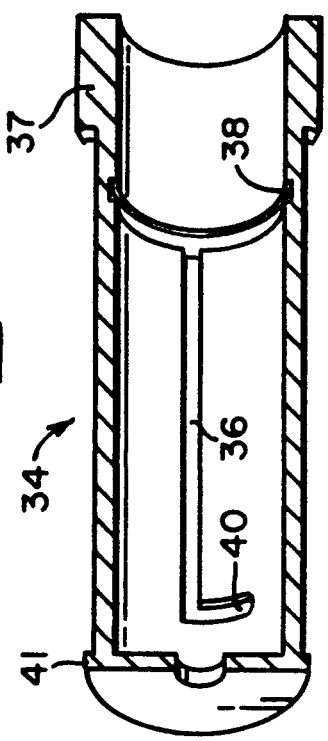
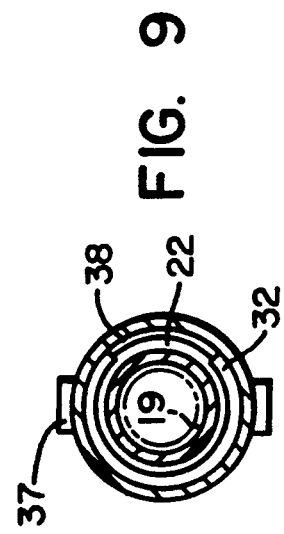

APPARATUS FOR SHIELDING A SYRINGE NEEDLE

FIELD OF THE INVENTION

This invention relates in general to an apparatus for shielding a syringe needle, and more particularly to an apparatus which can be locked in an extended position surrounding and shielding a syringe needle after use of the syringe. The apparatus includes a hollow sleeve and a needle shield, and utilizes a flexible snap ring within a groove of the needle shield as a locking means.

BACKGROUND OF THE INVENTION

Syringes have long been used to inject medications and other fluids into the bloodstream of patients. Syringes are also used to aspirate or withdraw various fluids from patients. These fluids include blood, for example.

When a syringe is used, the contact of the syringe needle with the patient can lead to contamination of the syringe, including the needle, with various contagious micro-organisms. The contaminated syringe and needle then pose a risk to anyone handling the syringe if the person accidentally pricks or contacts themself or someone else with the contaminated needle.

The danger of infection from contaminated needles and syringes has become of increased concern with the discovery of HIV (human immunodeficiency virus) which causes AIDS (Acquired Immune Deficiency Syndrome). The danger also exists for other infectious diseases and infections, such as hepatitis, streptococcal sepsis, tetanus, tuberculosis, Rocky Mountain Spotted Fever, and malaria.

The problem is especially relevant in the health care industry. Each year, 7% of hospital employees are involved in needle stick injuries, of which 60% are nurses. It is estimated that 57% of accidental needle sticks occur while attempting to recap the needle of a syringe or in disposal of the syringe. It is also estimated that in excess of $28.3 million is spent annually in the United States for the diagnosis and initial treatment of needle sticks.

Various strategies to deal with this problem have been attempted. One approach involves the use of some sort of cap to cover the syringe needle after use, to prevent contact with the needle. This cap can be as simple as the original plastic cap which is used to cover the needle prior to use. However, the motion required to replace the original needle cap allows for error resulting in needle contact. This is due to the relatively small diameter of the cap and the required movement of a hand toward the contaminated needle during cap replacement.

Other approaches provide for additional means for covering the needle, in the form of shields. Examples of shields are provided in U.S. Pat. Nos. 4,666,435; 4,871,355; 4,923,447; 4,998,920; and 5,098,403.

The goal of a shield is to provide a means for preventing pricks and contact with contaminated needles, without interfering with the normal usage of a syringe. The shield must also be easily manufactured in conjunction with a syringe or easily assembled onto an existing syringe if manufactured separately. Ways to make a shield in a cost-effective manner are also important.

Although various types of shields have been proposed, the severity of the AIDS epidemic and other infectious diseases/infections provides a continuous need for an apparatus for shielding a syringe needle which meets these requirements.

SUMMARY OF THE INVENTION

This continuous need is met, and the problem of contaminated needle pricks and contact overcome, by the needle shield and syringe assembly of the subject invention.

The main components of the needle shield include a hollow sleeve, needle shielding means, and a flexible snap ring. The hollow sleeve is mounted to a syringe housing. Any syringe can be adapted for use with the needle shield, including conventional medical syringes and syringes made for single use only (see co-pending U.S. patent application Ser. No. 07/978,181, filed Nov. 17, 1992, entitled "Plunger For Non-Reuseable Syringe", the contents of which are hereby incorporated by reference). The hollow sleeve has one or more radially extending projections and a groove into which the flexible snap ring can be inserted.

The needle shielding means is movably positioned on the hollow sleeve surrounding the syringe housing. In an extended position, the needle shielding means surrounds and shields the needle, while in a retracted position the needle shielding means leaves the needle exposed for use. To accomplish the movement of the needle shielding means, it is equipped with one or more longitudinally extending slots. Each of the radially extending projections of the hollow sleeve is slidably disposed within a corresponding slot on the needle shielding means.

When the snap ring is positioned within the groove on the hollow sleeve, the needle shielding means can be slid forward (toward and over the needle of the syringe) by pulling the syringe itself back toward the user as the projections of the hollow sleeve track along in the slots. At this time, the inner wall of the needle shielding means holds the snap ring securely in the groove of the hollow sleeve. When the needle shielding means is extended to fully cover the syringe needle, the groove on the inner wall of the needle shielding means is then positioned in line with the snap ring. The flexible snap ring extends outward into the groove in the needle shielding means, while remaining in part within the groove of the hollow sleeve. The tension forces of the snap ring trying to extend outwardly result in the secure and permanent positioning of the snap ring at this point. The snap ring therefore prevents further movement of the slidable needle shielding means, since the snap ring has locked into the grooves.

The syringe upon which the shield is utilized, whether it is a conventional medical syringe or a single use syringe, includes a hollow cylindrical syringe housing having an interior, and a hollow needle mounted to the housing. The needle is in fluid communication with the interior of the housing, and fluid can be drawn into the syringe housing or ejected therefrom by moving the plunger means which is positioned within the housing.

The hollow sleeve can be formed as an integral part of a syringe being manufactured, or can be attached to the housing of a syringe manufactured separately. Such attachment can be by any suitable permanent means, including glue or heat sealing. Preferably, the various parts of the syringe assembly, including the shield, are made of plastic to allow for manufacturing by injection molding. This allows for efficient and cost-effective production of the syringe and shield. Suitable plastics include clear lexan plastic, since a clear plastic allows the numbers on the syringe to be read through the shield components.

The resulting needle shield and syringe assembly can thus reduce the risk of accidental pricks and contact with contaminated needles. The movement of the needle shielding means is accomplished by a motion which is not directed toward the tip of the contaminated needle, and can be accomplished smoothly and easily with little effort. Thus, the needle shield and syringe assembly is practical in both manufacture and usage.

BRIEF DESCRIPTION OF THE FIGURES

These and other objects, features and advantages of this invention will be evident from the following detailed description of preferred embodiments when read in conjunction with the accompanying drawings in which:

FIG. 6 is a partially cut-away isometric view of one embodiment of a needle shielding means according to the subject invention;

FIG. 7 is a partially cut-away isometric view of a syringe and shield assembly according to one embodiment of the subject invention, with the needle shielding means in a retracted position;

FIG. 8 is a partially cut-away isometric view of the syringe and shield assembly shown in FIG. 7 with the needle shielding means in an extended position;

FIG. 9 is a cross-sectional view of the syringe and shield assembly shown in FIG. 8, illustrating the position of the snap ring within the grooves;

DETAILED DESCRIPTION OF THE INVENTION

Figure 1:
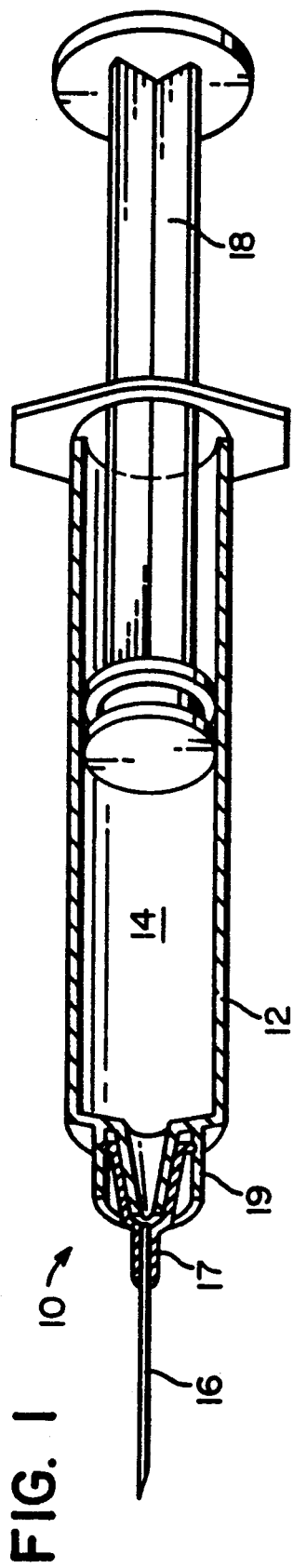
FIG. 1 is a partially cut-away isometric view of a syringe having a needle.

A typical syringe upon which the shield of the subject invention can be used is shown in FIG. 1. The syringe 10 has a hollow cylindrical housing 12 to which a hollow needle 16 is mounted. The hollow needle 16 is in fluid communication with the interior 14 of the housing 12. Movement of a plunger 18 positioned within the housing 12 allows the drawing of fluid into the syringe and the ejecting of fluid from the syringe. Syringe needles are generally marketed with a plastic-type bracket 17 on one end thereof. This plastic-type bracket mounts on the restricted end 19 of the syringe unit. The bracket may snugly slide over the restricted end, or the restricted end could be provided with grooves into which corresponding ridges on the bracket are twisted. Various means for connecting syringe needles are known in the art and can thus be used in the subject invention to mount a needle to a syringe housing.

Figure 2:
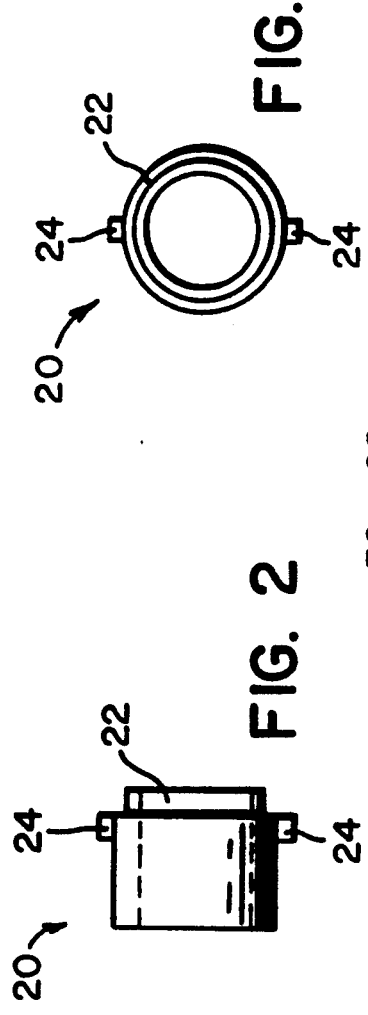
FIG. 2 is a front elevational view of one embodiment of a hollow sleeve according to the subject invention.
Figure 3:
FIG. 3 is a right side elevational view of the hollow sleeve shown in FIG. 2.
Figure 10:
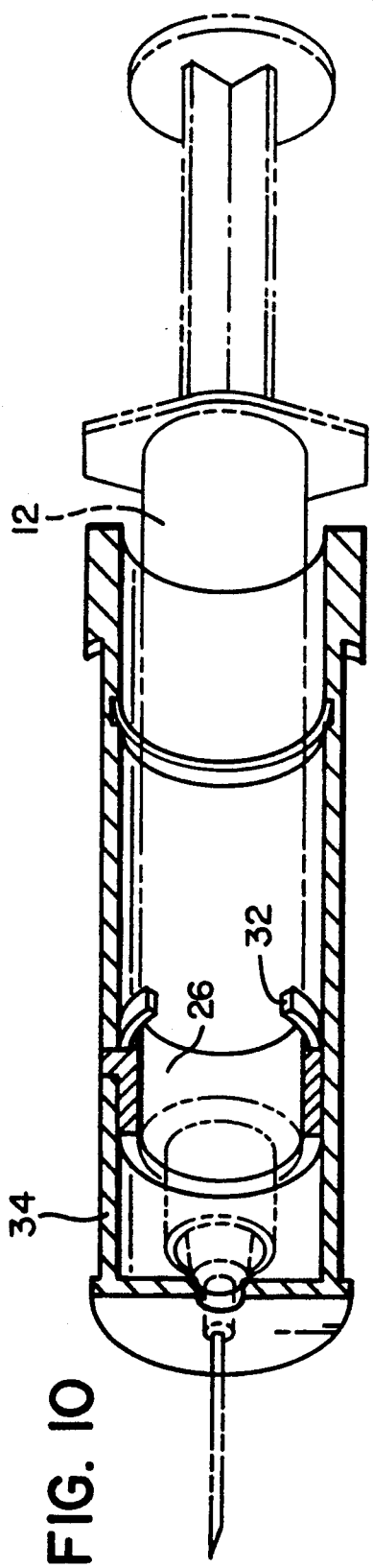
FIG. 10 is a partially cut-away isometric view of a syringe and shield assembly according to another embodiment of the subject invention, with the needle shielding means in a retracted position.
Figure 12:
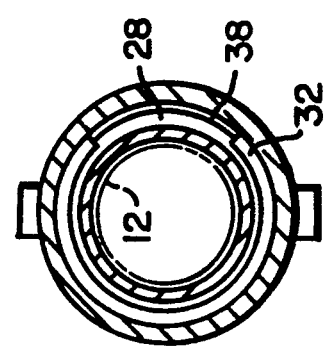
FIG. 12 is a cross-sectional view of the syringe and shield assembly shown in FIG. 11, illustrating the position of the snap ring within the grooves.
Figure 11:
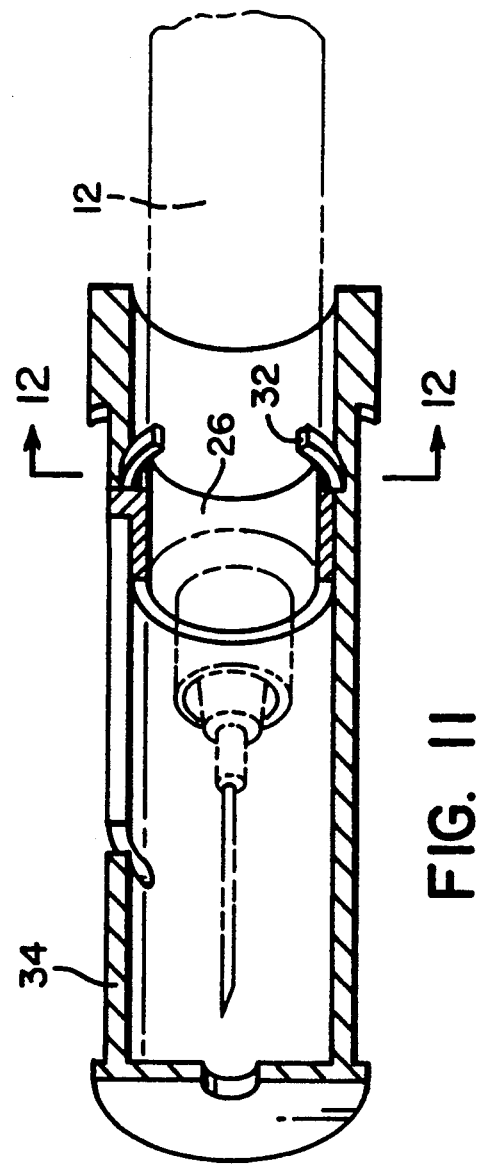
FIG. 11 is a partially cut-away isometric view of the syringe and shield assembly shown in FIG. 10 with the needle shielding means in an extended position.

The main components of the shield according to the subject invention are depicted in FIGS. 2–6. The shield includes a hollow sleeve 20 as shown in FIGS. 2 and 3. The hollow sleeve 20 is mounted to the housing of a syringe (see FIGS. 7–9). The sleeve 20 has two radially extending projections 24 and a groove 22 at one end, into which a flexible snap ring 32 (see FIG. 5) can be inserted. In an alternate embodiment of the hollow sleeve shown in FIG. 4, the groove 28 is not located at an end of the hollow sleeve 26 and only one radially extending projection 30 is utilized. The mounting of this embodiment of the hollow sleeve 26 to the housing of a syringe is shown in FIGS. 10–12. Generally, a single protrusion (and corresponding slot as discussed below) is most suitable on small syringes such as insulin syringes. The double protrusion is most suitable for larger, i.e., 3 cc or greater, syringes. It should be readily apparent, however, that one or more protrusions and corresponding slots can be utilized on any size syringe despite these preferences.

Figure 5:
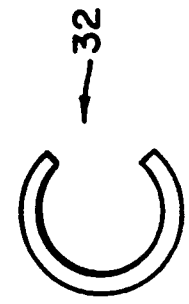
FIG. 5 is an elevational view of one embodiment of a snap ring according to the subject invention.

The shield assembly also includes a flexible snap ring 32 as shown in FIG. 5. Preferably, the snap ring is C-shaped and square or rectangular in cross-section so that the snap ring cannot be easily slid out of a groove into which it is inserted. The size of the snap ring is such that tensional forces hold it within the groove of the hollow sleeve and the interior wall of the needle shielding means (see below). As a result, when the snap ring becomes aligned with the groove in the interior wall of the needle shielding means, it extends outward (at the tips of the "C").

A needle shielding means is also included in the shield, as shown in FIG. 6. The needle shielding means 34 is tubular and preferably closed on one end, except for a hole which allows insertion of a needle. The closed end helps to contain any blood which may drip from the needle or syringe assembly after use. The hole or aperture for insertion of a needle is small and does not permit insertion of hands or fingers, which helps prevent needle sticks or contact. The closed end may be preformed or the end may be a cap-type that is snapped onto the end. In a further embodiment, the end of the needle shielding means may be open.

The needle shielding means has one or more longitudinally extending slots 36 on the interior wall thereof and an interior groove 38 at one end of the slots. The groove 38 allows extension of the snap ring when the needle shielding means is extended, locking into place and preventing further movement of the needle shielding means. Each of the radially extending protrusions of the hollow sleeve are slidably disposed within a corresponding slot, so that the needle shielding means can slide to an extended position to surround and shield the needle or to a retracted position surrounding the syringe housing and leaving the needle exposed for use. By placing the slots and groove on the interior of the needle shielding means, they cannot be tampered with. However, the shield will function if the slots and groove extend through the exterior surface of the needle shielding means, and this is also encompassed by the subject invention. The needle shielding means also has an aperture through the side thereof the size of the cross-section of the snap ring, positioned over the location of the hollow sleeve's groove when the needle shielding means is fully retracted. This aperture allows assembly of the shield components when a closed end needle shielding means is utilized. The hole is not necessary for assembly when the end of the needle shielding means is open, as discussed below.

A temporary locking means for releasibly locking the needle shielding means in its retracted position can also be included. This prevents premature extension of the needle shielding means which would result in locking of the shield into place over the needle, preventing use. As shown in FIG. 6, the temporary locking means preferably comprises one or more notches 40 formed in the interior of the needle shielding means extending off the ends of the slots. These notches are disposed substantially transversely relative to the slots, and are sized to receive the protrusions of the hollow sleeve. Rotation of the needle shielding means so that the protrusions are positioned within the notches prevents extension of the needle shielding means.

The needle shielding means can also be provided with a ring or lip 41 at its base (the end nearest the syringe needle) to help prevent slippage of a user's hand over the end of the shielding means to the needle. Slippage is also prevented by the finger grips 37 which allow a firm grasp on the needle shielding means during movement thereof.

The use of the needle shield, including the hollow sleeve, the needle shielding means, and the snap ring, is shown in FIGS. 7-12. The syringe is as shown in FIG. 1.

Referring to FIG. 7, the hollow sleeve 20 (see FIGS. 2 and 3) is mounted to the front restricted end 19 of the syringe housing 12. The needle shielding means 34 (see FIG. 6) is shown in the retracted position, with the snap ring 32 positioned in the groove 22 of the hollow sleeve 20. The protrusions 24 of the hollow sleeve 20 are temporarily locked in the notches 40 of the needle shielding means 34 extending off the ends of the slots 36.

Referring to FIG. 8, the needle shielding means 34 has been rotated and moved forward, allowing the protrusions 24 to be guided along in the corresponding slots 36. The extension of the needle shielding means 34 over the needle 16 has positioned the snap ring 32 in line with the interior groove 38 of the needle shielding means 34. As shown in FIG. 9, the snap ring 32 has extended to occupy both the groove 22 of the hollow sleeve and the groove 38 of the needle shielding means. This permanently locks the position of the needle shielding means.

Figure 4:
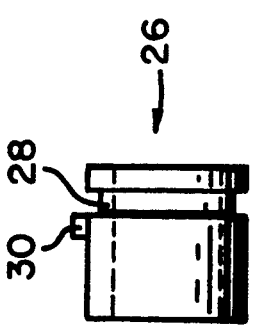
FIG. 4 is an elevational view of another embodiment of a hollow sleeve according to the subject invention.

Referring to FIG. 10, an alternate embodiment utilizing the single protrusion hollow sleeve 26 of FIG. 4 is shown. The hollow sleeve 26 is also positioned on the housing 12, but not on the restricted end. The needle shielding means 34 is shown in the retracted position, and in the extended position in FIG. 11. As shown in FIG. 12, the snap ring 32 extends to within the groove 38 of the needle shielding means from the groove 28 of the hollow sleeve. Since the hollow sleeve 26 is mounted on the housing 12, the housing 12 can be seen in this cross-sectional view.

Having thus described the components of the subject invention, it can be assembled as follows. In one embodiment, the hollow sleeve is mounted to the restricted end of the syringe housing. The hollow sleeve/housing is then inserted into the open end of the needle shielding means (one end of the needle shielding means is closed except for a small aperture for insertion of a needle). The diameter of the needle shielding means fits snugly about the syringe housing, but leaves enough room for passage of the protrusions. The protrusions are passed along the top part of the needle shielding means until they are disposed within their corresponding slots. To provide an even snugger fit of the needle shielding means and the syringe housing, the slots on the interior of the needle shielding means can be extended to the end of the needle shielding means to allow for insertion of the protrusions during assembly. The syringe can then be slid along the needle shielding means, using the protrusions within the slots as a guide. When the protrusions reach the end of the slots, the groove of the hollow sleeve is positioned beneath the hole or aperture in the needle shielding means. The snap ring is then inserted through the hole and into the hollow sleeve's groove. The syringe and shield assembly is then ready for use, once a needle is attached to the syringe. Any full extension of the needle shielding means will result in locking of the snap ring into the groove of the needle shielding means. The needle shielding means will thus be locked in a position which covers and shields the needle of the syringe.

Alternatively, a needle shielding means which is open on both ends, at least for assembly, can be utilized. In this embodiment, the syringe is inserted into the needle shielding means from the end. The needle shielding means is somewhat shorter than the syringe, and is positioned so that the restricted end of the syringe housing is exposed. The hollow sleeve is then attached to the syringe housing by suitable means (see above). After the hollow sleeve is attached, the snap ring is inserted into the groove of the hollow sleeve as the hollow sleeve is pulled within the needle shielding means. In this embodiment, an aperture for insertion of the snap ring is not necessary. However, one could also be utilized if the hollow sleeve is first slid into the needle shielding means before the snap ring is positioned. The syringe and shield assembly is then ready for use, once a needle is attached to the syringe. If desired, a cap can then be secured over the open end of the needle shielding device. As in the previous embodiment, a small hole or aperture in the cap would allow mounting of a needle to the syringe for use.

Although preferred embodiments have been depicted and described in detail herein, it will be apparent to those skilled in the relevant art that various modifications, additions, substitutions and the like can be made without departing from the spirit of the invention and these are therefore considered to be within the scope of the invention as defined in the following claims.

What is claimed is:

1. A syringe assembly comprising:
    a hollow cylindrical syringe housing having an interior and an exterior thereof;
    a hollow needle mounted to said housing in fluid communication with said interior of said housing;
    plunger means movably positioned within said housing for drawing fluid into said housing and for ejecting fluid from said housing;
    a hollow sleeve having an outer wall of substantially constant diameter, said hollow sleeve mounted to the exterior of said housing;
    needle shielding means having an inner wall, said needle shielding means movably positioned on said hollow sleeve and surrounding said housing with said needle shielding means being movable between an extended position surrounding and shielding said needle and a retracted position in which said needle is exposed for use; and
    a flexible snap ring, wherein said hollow sleeve has one or more projections radially extending from said outer wall and a first groove means in said outer wall for containing said snap ring within the diameter of said inner wall of said needle shielding means, and wherein said needle shielding means has one or more longitudinally extending slots and a second groove means in said inner wall for containing said snap ring as said snap ring extends beyond the diameter of said inner wall of said needle shielding means to occupy said first groove means and said second groove means concurrently, each of said one or more radially extending projections slidably disposed within a corresponding one of said one or more longitudinally extending slots, wherein as said needle shielding means is extended to surround and shield said needle, each of said one or more radially extending projections slides within said corresponding one of said one or more longitudinally extending slots, and wherein said snap ring is positioned in said first grove means with said needle shielding means in said retracted position and wherein said snap ring extends into said second groove means when said needle shielding means is extended to surround and shield said needle, said needle shielding means thereby being permanently locked into said extended position.

2. The syringe assembly of claim 1 further comprising temporary locking means for releasibly locking said needle shielding means in its retracted position so as to prevent premature permanent locking of the needle shielding means.

3. The syringe assembly of claim 2 wherein said temporary locking means comprises one or more notches formed in said needle shielding means, each of said one or more notches continuously extending from an end of a corresponding one of said one or more slots closest to said hollow needle, with each of said one or more notches being disposed substantially transversely relative to said corresponding one of said one or more slots and sized to receive said one of said one or more radially extending projections.

4. The syringe assembly of claim 1 wherein said housing has a restricted end to which said needle is mounted.

5. The syringe assembly of claim 4 wherein said hollow sleeve is mounted to said housing at said restricted end.

6. The syringe assembly of claim 1 wherein said second groove means in said inner wall of said needle shielding means continuously extends from an end of said one or more slots furthest from said hollow needle.

7. The syringe assembly of claim 1 wherein said needle shielding means has gripping means attached thereto.

8. A needle shield for use with a syringe, said needle shield comprising:
a hollow sleeve having an outer wall of substantially constant diameter, said hollow sleeve mountable to an exterior of a syringe housing;
needle shielding means having an inner wall, said needle shielding means movably positioned on said hollow sleeve for surrounding a syringe housing with said needle shielding means being movable between an extended position surrounding and shielding a needle of a syringe and a retracted position in which a needle of a syringe is exposed for use; and
a flexible snap ring, wherein said hollow sleeve has one or more projections radially extending from said outer wall and a first groove means in said outer wall for containing said snap ring within the diameter of said inner wall of said needle shielding means, and wherein said needle shielding means has one or more longitudinally extending slots and a second groove means in said inner wall for containing said snap ring as said snap ring extends beyond the diameter of said inner wall of said needle shielding means to occupy said first groove means and said second groove means concurrently, each of said one or more radially extending projections slidably disposed within a corresponding one of said one or more longitudinally extending slots, wherein as said needle shielding means is extended to surround and shield said needle, each of said one or more radially extending projections slides within said corresponding one of said one or more longitudinally extending slots, and wherein said snap ring is positioned in said first groove means with said needle shielding means in said retracted position and wherein said snap ring extends into said second groove means when said needle shielding means is extended to surround and shield a needle, said needle shielding means thereby being permanently locked into said extended position.

9. A method for shielding the needle of a syringe which method comprises:
mounting a hollow sleeve having an outer wall of substantially constant diameter onto an exterior of a housing of a syringe, said hollow sleeve having one or more projections radially extending from said outer wall and a first groove means in said outer wall for containing a snap ring;
movably positioning a needle shielding means having an inner wall on said hollow sleeve wherein said needle shielding means is movable between an extended position surrounding and shielding a needle of a syringe and a retracted position in which a needle of a syringe is exposed for use, said needle shielding means having one or more longitudinally extending slots and a second groove means in said inner wall for containing a snap ring, wherein each of said one or more radially extending projections is slidably disposed within a corresponding one of said one or more longitudinally extending slots;
positioning a snap ring within said first groove means when said needle shielding means is in its retracted position, said snap ring being contained within the diameter of said inner wall of said needle shielding means; and
extending said needle shielding means to surround and shield a needle of said syringe, wherein as said needle shielding means is extended, each of said one or more radially extending projections slides within said corresponding one of said one or more longitudinally extending slots, and wherein said snap ring extends beyond the diameter of said inner wall of said needle shielding means into said second groove means upon said extension of said needle hisleding means, said snap ring thereby occupying said first groove means and said second groove means concurrently and thereby permanently locking said needle shielding means into said extended position.

* * * * *

UNITED STATES PATENT AND TRADEMARK OFFICE
CERTIFICATE OF CORRECTION

PATENT NO. : 5,290,255
DATED : March 1, 1994
INVENTOR(S) : Vallelunga et al.

It is certified that error appears in the above-indentified patent and that said Letters Patent is hereby corrected as shown below:

In column 7, line 19, claim 1, change "grove" to -- groove --.

In column 8, line 62, claim 9, change "hisleding" to -- shielding --.

Signed and Sealed this

Twelfth Day of July, 1994

Attest:

BRUCE LEHMAN

*Attesting Officer*  *Commissioner of Patents and Trademarks*